(12) United States Patent
Small, Jr. et al.

(10) Patent No.: US 8,268,307 B2
(45) Date of Patent: Sep. 18, 2012

(54) ENHANCING EFFICACY OF VACCINES ADMINISTERED VIA THE RESPIRATORY TRACT

(75) Inventors: Parker A. Small, Jr., Gainesville, FL (US); Bradley S. Bender, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 293 days.

(21) Appl. No.: 12/525,735

(22) PCT Filed: Mar. 19, 2008

(86) PCT No.: PCT/US2008/057428
§ 371 (c)(1),
(2), (4) Date: Dec. 14, 2009

(87) PCT Pub. No.: WO2008/127833
PCT Pub. Date: Oct. 23, 2008

(65) Prior Publication Data
US 2010/0104562 A1    Apr. 29, 2010

(51) Int. Cl.
*A61K 39/145* (2006.01)
*A61K 39/395* (2006.01)
(52) U.S. Cl. .............. 424/130.1; 424/184.1; 424/204.1; 424/209.1

(58) Field of Classification Search ................. None
See application file for complete search history.

(56) References Cited

U.S. PATENT DOCUMENTS
2005/0271728 A1    12/2005    Nomura et al.

OTHER PUBLICATIONS

Hanson et al (Bacterial Vaccines and Local Immunity, Ann. Sclavo., 1986, n. 1-2, pp. 233-237, 1986).*
Savilahti et al (Journal of Clinical Immunology 8:89-94, 1988).*
Schmidt et al (New England Journal of Medicine 280:188-193, 1969).*
Ali et al (Journal of Applied Sciences Research 1:401-404, 2005).*
Cox et al. Influenza Virus: Immunity and Vaccination Strategies. Comparison of the Immune Response to Inactivated and Live, Attenuated Influenze Vaccines. Scandinavian Journal of Immunology, Jan. 2004, vol. 59, No. 1 pp. 1-15 (p. 5, col. 1, para 5; p. 8 table 4; p. 10 col. 1 para 3).

* cited by examiner

*Primary Examiner* — Mary E Mosher
(74) *Attorney, Agent, or Firm* — Timothy H. Van Dyke; Beusse, Wolter, Sanks, Mora & Maire, P.A.

(57) ABSTRACT

Disclosed herein are vaccine compositions comprising live attenuated virus with anti-antibody to improve efficacy. Specifically exemplified herein is a composition comprising live attenuated cold adapted influenza virus and an enhancing amount of IgG anti-IgA antibody to temporarily inactivate IgA defenses. Also disclosed herein are methods of immunizing a subject to protect against influenza comprising administering compositions taught herein.

9 Claims, No Drawings

ENHANCING EFFICACY OF VACCINES ADMINISTERED VIA THE RESPIRATORY TRACT

GOVERNMENT SUPPORT

The United States Government, as represented by the Department of Veterans Affairs, has rights in the subject invention.

BACKGROUND

Influenza, commonly known as the flu, is an infectious disease of birds and mammals caused by an RNA virus of the family Orthomyxoviridae (the influenza viruses). In humans, common symptoms of influenza infection are fever, sore throat, muscle pains, severe headache, coughing, weakness, and fatigue. (Merck Manual Home Edition. Influenza: Viral Infections). In more serious cases, influenza causes pneumonia, which can be fatal, particularly in young children and the elderly. Sometimes confused with the common cold, influenza is a much more severe disease and is caused by a different type of virus. Eccles, R (2005). "Understanding the symptoms of the common cold and influenza". Lancet Infect Dis 5 (11): 718-25. Although nausea and vomiting can be produced, especially in children, (Merck Manual Home Edition. Influenza: Viral Infections) these symptoms are more characteristic of the unrelated gastroenteritis, which is sometimes called "stomach flu" or "24-hour flu". Seasonal Flu vs. Stomach Flu by Kristina Duda, R.N.; accessed Mar. 12, 2007 (Website: "About, Inc., A part of The New York Times Company").

Flu spreads around the world in seasonal epidemics, killing millions of people in pandemic years and hundreds of thousands in non-pandemic years. Three influenza pandemics occurred in the 20th century and killed tens of millions of people, with each of these pandemics being caused by the appearance of a new strain of the virus in humans. Often, these new strains result from the spread of an existing flu virus to humans from other animal species. Since it first killed humans in Asia in the 1990s, a deadly avian strain of H5N1 has posed the greatest risk for a new influenza pandemic.

Vaccinations against influenza are most commonly given to high-risk humans in industrialized countries (WHO position paper: influenza vaccines *WHO weekly Epidemiological Record* 19 Aug. 2005, vol. 80, 33, pp. 277-288), and to farmed poultry (Villegas, P (1998). "Viral diseases of the respiratory system". *Poult Sci* 77 (8): 1143-5. PMID 9706079). The most common human vaccine is the trivalent flu vaccine that contains purified and inactivated material from three viral strains. Typically this vaccine includes antigenic material from two influenza A virus subtypes and one influenza B virus strain and is given by intramuscular injection. A vaccine formulated for one year may be ineffective in the following year; the influenza virus changes rapidly over time and hence annually different strains become dominant.

Another vaccine, live attenuated, cold-adapted influenza vaccine (LACAIV) is becoming widely recognized as a better alternative to conventional vaccines, especially in children ages 1-5 years old. One clear advantage is that this vaccine can be administered via a nasal spray into the upper respiratory tract as opposed to intramuscular injection. Further, LACAIV has theoretical advantages over intramuscular influenza shots in that it induces sIgA antibody which prevents flu infection of the upper respiratory tract (Renegar, Kathryn B. and Small, Parker A., Jr., Immunoglobulin A mediation of murine nasal anti-influenza virus immunity. *J. of Virology*, 65:2146-2148, 1991), cell mediated immunity which enhances recovery (Bender, B. S. Coroghan, T., Liping, Z and Small, P. A. Jr., Transgenic mice lacking major histocompatibility complex-restricted class 1 T-cells have delayed viral clearance and increased mortality following influenza virus challenge, *J. Exp. Med.* 175:1143-1145, 1992), and serum IgG antibody which has long been known to prevent infection of the lungs (viral pneumonia) (Loosli, C. G., D Hamre, and B. D. Berlin, Airborne influenza virus A infection in immunized animals, *Trans. Ass. Amer. Physicians* 66:222-230,1953), but not to prevent infection of the upper respiratory tract (Ramphal, R. Cogliano, R. C. Shands, J. W., Jr. and Small, P. A., Jr., Serum antibody prevents murine influenza pneumonia but not influenza tracheitis, *Infect. Immun.* 25:992997, 1979). These theoretical advantages of LACAIV, however, are not always observed in field trials. In fact, it has been shown that in individuals age 18 to 46 years old, LACAIV is significantly less effective than intramuscular injection of an inactivated vaccine. (Ohmit et al., Prevention of Antigenically Drifted Influenza by Inactivated and Live Attenuated Vaccines, *N Engl J Med*, 355:2513-2522, 2006). This problem is perplexing and casts a shadow over the use of LACAIV as a viable vaccine alternative for adults.

SUMMARY

According to one embodiment, the subject invention provides a solution to the reduced efficacy of LACAIV in older children and adults which can also be applied to other vaccines administered to the upper respiratory tract. The inventors have observed that LACAIV is likely neutralized in adults by the action of secretory IgA antibody in the nasal passages. Because of this neutralization, viral growth of the attenuated vaccine is limited, and the necessary immunogenic dose of virus is not achieved. Furthermore, the inventors have developed an improvement to the LACAIV to overcome this problem. Accordingly, in one embodiment, the invention is directed to a vaccine administered via the respiratory tract, such as LACAIV, which further comprises an effective amount of anti-IgA antibody (anti-antibody). The addition of anti-antibody serves to neutralize or inactivate the activity of sIgA antibody to the influenza virus, which will allow a sufficient amount of the vaccine virus to replicate so as to be able to induce an acceptable level of immunity.

As will be further noted below, anti-antibody can be added to vaccines directed to other viruses and microorganisms which are configured for administration in the upper respiratory tract such as viral vectored gene therapy. Furthermore, the LACAIV is designed as a vaccine against seasonal influenza (i.e. H3N2, H1N1 $ B). An additional advantage of the LACAIV/anti-antibody embodiment is that it may protect against other influenza types, such as pandemic influenza (e.g. H5N1). This is because the sIgA antibody induced by LACAIV can be cross-reactive (Waldman, R. H., F. M. Wigley and P. A. Small, Jr. Specificity of Respiratory Secretion Antibody against Influenza Virus, *J. Immun*, 106:1477-1483, 1970), whereas serum IgG antibody is specific.

DETAILED DESCRIPTION

Flu-mist is a LACAIV product manufactured and marketed by MedImmune Vaccines, Inc. Gaithersburg, Md. 20878. One embodiment of the subject invention relates to a Flu-mist product further comprising an enhancing amount of anti-antibody. An enhancing amount of anti-antibody in a vaccine referred to herein relates to an amount which serves to increase the efficacy of the vaccine. Increased efficacy relates to a lesser number of flu cases or symptoms, or both, in vaccine/anti-antibody versus vaccine alone; increased serum antibody titer against target pathogen in vaccine/anti-antibody versus vaccine alone; or a combination of the foregoing. The Ohmit et al. reference referred to above provides background on this issue.

In other embodiments, the subject invention pertains to a viral vaccine designed for intranasal delivery which comprises anti-antibody. For example, viral vaccines against other diseases including but not limited to the common cold, RSV, SARS, and virus vectored (e.g., AAV or adeno vectored) cystic fibrosis therapy can be combined with anti-antibody to temporarily inactivate IgA immunity in the upper respiratory passages. The anti-antibody may be of any immunoglobulin class (IgG, IgA, IgM, IgD, IgE) or a synthetic molecule, and may be produced in murine, equine, porcine, bovine, canine, feline, ovine or other species. It also could be produced as a monoclonal antibody (e.g. murine antibody), or humanized version of an antibody. In a specific embodiment, the anti-antibody is IgG anti-human IgA.

Another embodiment of the invention pertains to a method of immunizing a subject against a target pathogen. The method comprises administering intranasally a therapeutically effective amount of a composition comprising a vaccine and anti-antibody to the subject. A therapeutically effective amount comprises that amount to induce an immune response in the recipient. Preferably, the therapeutically effective amount is an amount to provide protective immunity against the target pathogen. The vaccine may be tailored to immunize against viruses, bacteria, mycobacteria, fungi and protozoa in which immunization is neutralized by sIgA in the upper respiratory passages.

In one embodiment, the vaccine may comprise live attenuated virus, inactive virus, or viral antigens (e.g., viral polypeptides or nucleotides), or a combination thereof. In a specific embodiment, the composition comprises LACAIV and anti-antibody. In a more specific embodiment, the composition comprises an enhancing amount of anti-antibody.

The anti-antibody may be obtained from a number of suitable sources. Examples of sources include, but are not limited to, blood from immunized animals, colostrum from immunized animals, peptide synthesis, recombinant production and the like. In a specific embodiment, the source is bovine colostrom of animals immunized with human IgA. Using bovine colostrom as a source has an advantage in that every human who consumed cow's milk in their youth and perhaps adulthood has undoubtedly had their upper respiratory passages exposed to bovine IgG antibody. Thus, bovine colostrom provides an exceptionally safe source of product, as undesired side effects will be minimal.

In another embodiment, the subject invention pertains to an article of manufacturer comprising vaccine and anti-antibody. The article of manufacture can be a vial, a syringe, a vaporizer or a nasal spray applicator. In an alternative embodiment, the subject invention pertains to a kit comprising a nasal spray applicator comprising vaccine and a nasal spray applicator comprising IgG anti-IgA antibody.

Those skilled in the art will appreciate that other components may be added to composition embodiments suitable for the mode of administration. For example, vaccines often include adjuvant, pharmaceutically acceptable carriers, water, etc. For example, U.S. Pat. Nos. 7,112,332; 6,780,421; 6,613,321; 6,740,325; and 6,562,352 teach various components that may be added to vaccines.

The disclosures of the cited patent documents, publications and references are incorporated herein in their entirety to the extent not inconsistent with the teachings herein. It should be understood that the examples and embodiments described herein are for illustrative purposes only and that various modifications or changes in light thereof will be suggested to persons skilled in the art and are to be included within the spirit and purview of this application.

What is claimed is:

1. A composition comprising live attenuated cold adapted influenza virus and anti-antibody.

2. A composition comprising a vaccine and anti-antibody.

3. The composition of claim 2, wherein said vaccine comprises live attenuated virus, inactive virus, or viral antigens.

4. The composition of claim 2, wherein said anti-antibody is IgG anti-IgA antibody.

5. The composition of claim 2 wherein said anti-antibody is IgM anti-IgA antibody.

6. A method of vaccinating a subject to protect against influenza, said method comprising administering to said subject a therapeutically effective amount of a composition comprising live attenuated cold adapted influenza virus and anti-antibody.

7. The method of claim 6, wherein said composition is administered intranasally.

8. In a method of vaccinating a subject to protect against a target pathogen comprising administering to said subject a vaccine intranasally, the improvement comprising co-administering anti-IgA with said vaccine.

9. A method of vaccinating a subject to protect against a target pathogen, said method comprising administering to said subject a therapeutically effective amount of a composition comprising vaccine and anti-antibody.

* * * * *